United States Patent [19]
Gerecke et al.

[11] 3,966,737
[45] June 29, 1976

[54] FLUORO-SUBSTITUTED DIBENSO [b,f] THIEPINS

[75] Inventors: Max Gerecke, Reinach; Jean-Pierre Kaplan, Le Plessis Robinson; Emilio Kyburz, Reinach, all of Switzerland

[73] Assignee: Hoffmann-La Roche Inc., Nutley, N.J.

[22] Filed: May 17, 1974

[21] Appl. No.: 471,101

Related U.S. Application Data

[63] Continuation-in-part of Ser. No. 378,733, July 12, 1973, abandoned.

[30] Foreign Application Priority Data
Mar. 30, 1973 Switzerland.......................... 4606/73
Jan. 16, 1974 Switzerland............................ 568/74

[52] U.S. Cl............................. 260/268 TR; 424/250
[51] Int. Cl.$^2$........................................ C07D 409/04
[58] Field of Search............................. 260/268 TR

[56] References Cited
UNITED STATES PATENTS

| | | |
|---|---|---|
| 3,563,993 | 2/1971 | Schindler et al............. 260/268 TR |
| 3,583,989 | 6/1971 | Fouche et al................ 260/268 TR |
| 3,600,391 | 8/1971 | Mastursi et al.............. 260/268 TR |
| 3,681,354 | 8/1972 | Mastursi et al.............. 260/268 TR |
| 3,699,104 | 10/1972 | Schindler et al............. 260/268 TR |
| 3,725,409 | 4/1973 | Protiva ........................ 260/268 TR |
| 3,787,444 | 1/1974 | Gosteli........................ 260/268 TR |

FOREIGN PATENTS OR APPLICATIONS
1,093,910   12/1964   United Kingdom

OTHER PUBLICATIONS
Umio et al. Chemical Abstracts vol. 75, pp. 76847a and 76849c (1971).

*Primary Examiner*—Raymond V. Rush
*Assistant Examiner*—Jose Tovar
*Attorney, Agent, or Firm*—Samuel L. Welt; George M. Gould; William G. Isgro

[57] ABSTRACT

Compounds of the formulas

I and

Ia wherein R, $R_1$, $R_2$, $R_3$, $R_4$ and $n$ are as hereinafter set forth,
are described. The compounds of formulas I and Ia are prepared inter alia by the reaction of the corresponding dibenzo[b,f] thiepin and the corresponding piperazine compound. The end products are useful as neuroleptic agents.

9 Claims, No Drawings

FLUORO-SUBSTITUTED DIBENSO[B,F] THIEPINS

CROSS-REFERENCE TO RELATED APPLICATIONS

This application is a continuation-in-part of application Ser. No. 378,733, filed July 12, 1973 now abandoned.

BRIEF SUMMARY OF THE INVENTION

The invention relates to tricyclic compounds of the formulas

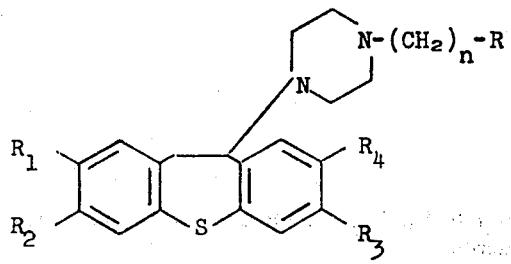

I and

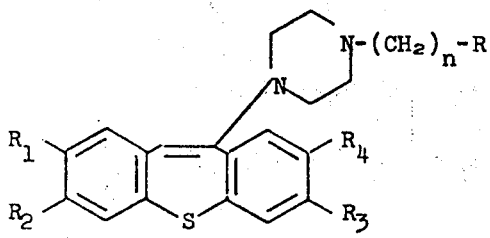

Ia

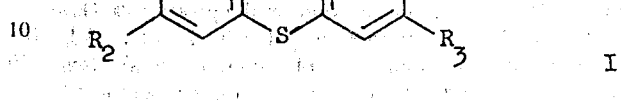

I and wherein $n$ is an integer from 1 to 3; R is hydrogen or, when $n$ is 2 or 3, is also hydroxy or an alkanoyloxy group of 2–18 carbon atoms; one of $R_1$ and $R_2$ is hydrogen and the other is methyl, methoxy, dimethylsulfamoyl, fluoro, chloro or trifluoromethyl; and one of $R_3$ and $R_4$ is hydrogen and the other is methyl, methoxy, methylthio, dimethylsulfamoyl, chloro, fluoro or trifluoromethyl, provided that at least one of $R_1$, $R_2$, $R_3$ and $R_4$ is fluoro, and pharmaceutically acceptable acid addition salts thereof. The end products are useful as neuroleptic agents.

As used herein, the term "alkanoyloxy" denotes a straight chain or branched chain group. Exemplary of such groups are acetoxy, pivaloyloxy, pentanoyloxy, and the like. Preferred are those groups wherein the alkanoyloxy is a long chain group; preferably from 6–18 carbon atoms, for example, hexanoyloxy, heptanoyloxy, octanoyloxy, nonanoyloxy, decanoyloxy, undecanoyloxy, dodecanoyloxy, tetradecanoyloxy, hexadecanoyloxy, octadecanoyloxy, or the like.

It has been discovered that the compounds of formulas I and Ia of the invention and their pharmaceutically acceptable acid addition salts demonstrate strong central depressant and neuroleptic activity. They can, therefore, for example, be utilized for the treatment of acute or chronic schizophrenia, as well as tranquilizers. Advantageously, the compounds of the invention demonstrate no or very weak cataleptic side effects, so that no or only insignificant motor disturbances are observed. Preferred compounds of the invention are those of formula I, as well as their salts with pharmaceutically acceptable acids. Preferred compounds of formulas I and Ia of the invention are those wherein $R_3$ or $R_4$ is fluoro, as well as their salts with pharmaceutically acceptable acids. Preferred are also those compounds of formula I and Ia, wherein $R_3$ is chloro and $R_4$ is fluoro Ia wherein $n$ is an integer from 1 to 3; R is hydrogen or, when $n$ is 2 to 3 is also hydroxy or an alkanoyloxy group of 2–18 carbon atoms, and wherein further one of $R_1$ and $R_2$ is hydrogen and the other is methyl, methoxy, methylthio, dimethylsulfamoyl, chloro, fluoro or trifluoromethyl, and one of $R_3$ and $R_4$ is hydrogen, and the other is methyl, methoxy, methylthio, dimethylsulfamoyl, chloro, fluoro or trifluoromethyl, provided that at least one of $R_1$, $R_2$, $R_3$ and $R_4$ is fluoro, and pharmaceutically acceptable acid addition salts thereof. The end products are useful as neuroleptic agents.

DETAILED DESCRIPTION OF THE INVENTION

The invention relates to tricyclic compounds of the formula as well as their salts with pharmaceutically acceptable acids.

An interesting group of the compounds of the invention are those of formulas I and Ia, wherein $R_1$ or $R_2$ is methyl, methoxy, methylthio, dimethylsulfamoyl or trifluoromethyl and $R_3$ or $R_4$ is fluoro, as well as their salts with pharmaceutically acceptable acids. Another preferred group of compounds of the invention are those of formulas I and Ia, wherein the group —$(CH_2)_n$—R is methyl or 3-hydroxypropyl, as well as the pharmaceutically acceptable salts of such compounds. Preferred compounds of the invention are 1-(2-chloro-7-fluoro-10,11-dihydro-dibenzo[b,f]thiepin-10-yl)-4-methylpiperazine, 1-(3-chloro-8-fluoro-10,11-dihydro-dibenzo[b,f]thiepin-10-yl)-4-methylpiperazine, 4-(2-chloro-8-fluoro-10,11-dihydro-dibenzo[b,f]thiepin-10-yl)-1-piperazine-propanol, 1-(8-fluoro-10,11-dihydro-2-methyl-dibenzo[b,f]thiepin-10-yl)-4-methylpiperazine, and salts thereof with pharmaceutically acceptable acids.

The 10,11-saturated compounds of formula I and their addition salts with pharmaceutically acceptable acids can be prepared according to the processes hereinafter described:

a. A compound of the formula

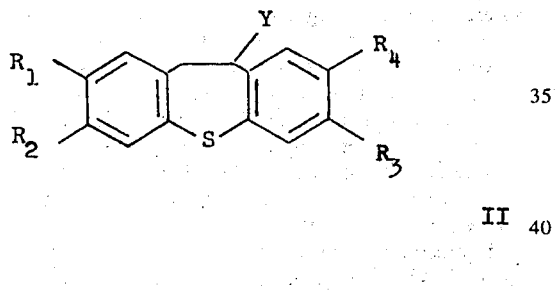

II wherein $R_1$, $R_2$, $R_3$ and $R_4$ are as hereinbefore described, and Y is a leaving group,
is reacted with a compound of the formula

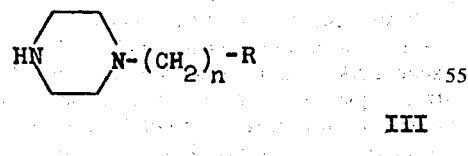

III wherein n and R are as hereinbefore described,
or
b. A compound of the formula

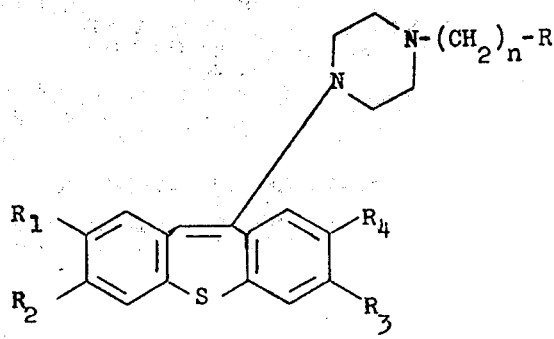

IV wherein R, $R_1$, $R_2$, $R_3$ and $R_4$ and n are as hereinbefore described,
is reduced; or c. A compound of the formula

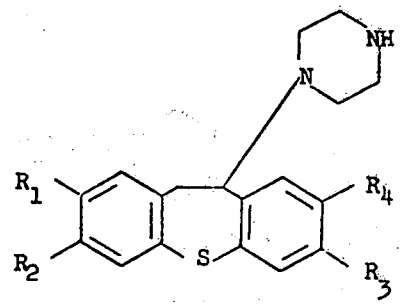

V wherein $R_1$, $R_2$, $R_3$ and $R_4$ are as hereinbefore described,
is reacted with ethylene oxide, propylene oxide or a compound of the formula $$Y-(CH_2)_n-R \qquad VI$$

wherein Y, n and R are as hereinbefore described; or
d. for the preparation of compounds of formula I wherein R is an alkanoyloxy group with up to 18 carbon atoms, a compound of the formula

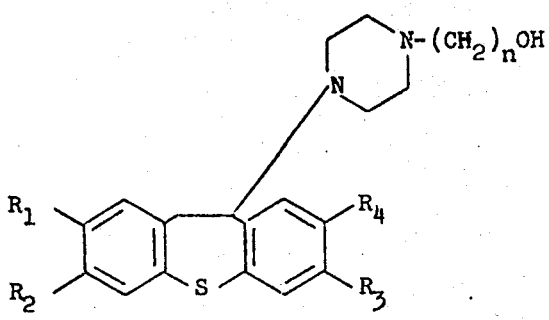

VII wherein $R_1$, $R_2$, $R_3$, $R_4$ and $n$ are as hereinbefore described,
is reacted with an acid of the formula $$R_5COOH \qquad \text{VIII}$$

wherein $R_5$ is lower alkyl of up to 17 carbon atoms, or is reacted with a reactive derivative of such an acid, and if desired, the resulting products can be converted to their pharmaceutically acceptable acid addition salts.

The 10,11-unsaturated compounds of formula Ia and their salts with pharmaceutically acceptable acids can be prepared by a process as hereinafter described, that is, a compound of the formula

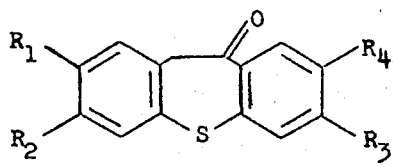

IX wherein $R_1$, $R_2$, $R_3$ and $R_4$ are as hereinbefore described,
is reacted with a compound of the formula

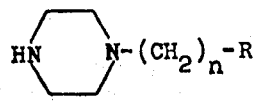

III wherein $n$ and R are as hereinbefore described.

If desired, a compound of formula Ia wherein R is hydroxy, can be esterified, and, if desired, the resulting products can be converted to a pharmaceutically acceptable acid addition salt.

The leaving group Y of the starting material of formula II is preferably halogen or alkyl-substituted or aryl-substituted sulfonyloxy. Preferably, the alkyl group of the sulfonyloxy substituent is lower alkyl, such as methyl, and preferably the aryl group of the sulfonyloxy substituent is phenyl or p-tolyl. The halogen substituent is preferably chlorine or bromine.

The Y group of the starting material of formula II can, for example, be introduced in the following manner:

When Y is to be halogen, the corresponding 10-hydroxy compound is reacted with an appropriate halogenating agent, for example, thionyl chloride, thionyl bromide, or with a hydrogen halide in the presence of a dehydrating agent, for example, hydrogen chloride and calcium chloride.

When Y is to be alkyl-substituted or aryl-substituted sulfonyloxy, the corresponding 10-hydroxy compound is reacted with an alkyl-substituted or aryl-substituted sulfonic acid halide, for example, the chloride.

If desired, the esters of formula III can be prepared by reacting the corresponding N-(hydroxyalkyl)-piperazine of formula III wherein the second nitrogen is protected, for example, by benzyl or benzyloxycarbonyl with the corresponding alkanecarboxy acid halide and subsequent hydrogenolytic cleavage of the protecting group.

The aforementioned reaction of the compounds of formulas II and III in accordance with the invention can be conducted without the addition of a solvent. If, however, a solvent is utilized, it preferably is an organic solvent, for example, an aromatic hydrocarbon such as benzene or toluene, a lower alkanol such as methanol or ethanol, a chlorinated hydrocarbon such as methylene chloride, trichloroethylene, chloroform, carbon tetrachloride or chlorobenzene, an aliphatic or cyclic ether such as diethyl ether, tetrahydrofuran or dioxane, or dimethylformamide or dimethylsulfoxide. The reaction temperature suitably is in the range of from about 30° to about 200°; preferably, the temperature of the reaction is in the range of from about 60° to about 150°. Advantageously, the reaction is carried out in the presence of an acid-binding agent, for example, in the presence of an alkali carbonate such as potassium carbonate or in the presence of an excess of the compound of formula III.

The starting enamines of formula IV are likewise end products of formula Ia. The enamines of formula IV are prepared in accordance with the invention by reacting the corresponding 10-oxo compound of formula IX with a compound of the above formula III. For example, the reaction can be carried out in the presence of a strong acid in an aromatic solvent with heating, for example, at a temperature in the range of from about 80° to about 150°. As the acid, there can be utilized, for example, mineral acids such as sulfuric acid or hydrochloric acid or a strong organic acid such as methanesulfonic acid or p-toluenesulfonic acid. As the aromatic solvents, there can be utilized, for example, preferably, benzene, toluene, or o-, m-or p-xylene. By heating, there is formed an azeotrope between the solvent and the water which is formed in the reaction, which can be distilled. The water formed can also be removed by the addition of a dehydrating agent such as titanium tetrachloride or the like.

An obtained enamine alcohol of formula IV, that is, a compound of formula IV, wherein R is hydroxy, can be converted to the corresponding ester of formula IV, preferably by reacting the enamine alcohol of formula IV with the corresponding alkane carboxylic acid in the presence of a non-acidic dehydrating agent, for example, dicyclohexylcarbodiimide or carbonyldiimidazole.

In accordance with the invention, the reduction of the enamines of formula IV is preferably carried out by treatment with an alkali metal borohydride in the presence of a strong acid. As the alkali metal borohydride, preferably there can be used sodium or potassium borohydride, especially sodium borohydride. It is also possible to utilize lithium borohydride. The strong acid can be an organic or an inorganic acid. As an organic acid, there can be utilized a straight or branched chain lower mono- or dicarboxylic acid with up to 4 carbon atoms, which can be substituted by halogen, for example, formic acid, acetic acid, trichloroacetic acid, trifluoroacetic acid, propionic acid, isobutyric acid, oxalic acid, and the like. Preferred is acetic acid; especially preferred is oxalic acid. As an inorganic acid, there can be utilized, for example, sulfuric acid, hydrohalic acid; especially hydrochloric acid, and the like. A preferred inorganic acid is concentrated sulfuric acid. The enamines of formula IV are unstable in the presence of water. It is, therefore, indicated that the reduction suitably be carried out in the absence of water. The reaction preferably is carried out in anhydrous acid or only in such acids where should they contain some water, this water is not released, for example, concentrated sulfuric acid. The reaction with the alkali metal borohydride and a strong acid can advantageously be carried out in an ether such as diethyl ether, tetrahydrofuran, dioxane, diethyleneglycoldimethyl ether (diglyme) or dimethoxyethane, at a temperature in the range of between about room temperature and the reflux temperature of the reaction mixture. Preferably, the reaction is carried out at the reflux temperature. In accordance with the invention, the reduction of an enamine of formula IV can also be carried out by other methods, for example, by treatment with formic acid or with zinc and acetic acid. The foregoing reaction is conveniently carried out at a temperature between about room temperature and the reflux temperature of the solvent; preferably at the reflux temperature.

The starting materials of formula IX as well as the corresponding 10-hydroxy compounds referred to herein are known compounds or can be prepared according to known procedures.

The starting compounds of formula V can be prepared, for example, by the reaction of a compound of formula II with a mono-N-protected piperazine such as N-carbethoxy-piperazine. The condensation product is subsequently subjected to alkaline saponification, e.g. with the aid of aqueous alkali.

An ester of formula VI can be prepared from the corresponding hydroxyalkyl compound of formula VI by reacting with the corresponding alkanecarboxylic acid halide.

In accordance with the invention, the reaction of a starting material of formula V with ethyleneoxide, propyleneoxide or a compound of formula VI is carried out conveniently in an inert organic solvent such as in an aromatic hydrocarbon, for example, benzene or toluene, a chlorinated hydrocarbon, for example, chloroform or the like, an ether, for example, dioxane or dimethoxyethane, a lower alkanol such as methanol or ethanol, a ketone such as acetone or methylethyl ketone, or dimethylformamide or dimethylsulfoxide. The temperature of the reaction mixture is preferably in the range of from about room temperature to about the boiling point of the reaction mixture. Utilizing a starting material of formula VI, the reaction favorably is conducted in the presence of an acid-binding agent, for example, in the presence of an alkali metal carbonate, such as sodium or potassium carbonate, or in the presence of an inert organic base such as triethylamine. As the acid-binding agent there can likewise be utilized an excess of the starting material of formula V.

In accordance with the invention, the esterification of a starting material of formula VII with an acid of formula VIII can be carried out conveniently at a temperature in the range of from about 50° to about 150° with a reactive derivative of a lower-alkanecarboxylic acid, for example, with the corresponding acid chloride or acid anhydride. The esterification can also be carried out by reaction with an alkanecarboxylic acid in the presence of a strong acid catalyst such as sulfuric acid or p-toluenesulfonic acid, or in the presence of a dehydrating agent, for example, dicyclohexylcarbodiimide or carbonyldiimidazole. Preferably, the etherification is conducted in an organic solvent, for example, benzene, toluene or pyridine.

The obtained bases of formulas I and Ia form salts with inorganic as well as with organic acids, for example, with hydrohalic acids such as hydrochloric acid, hydrobromic acid or hydroiodic acid, with other mineral acids such as sulfuric acid, phosphoric acid or nitric acid, also with organic acids such as acetic acid, citric acid, camphorsulfonic acid, methanesulfonic acid, toluene-sulfonic acid, salicyclic acid, ascorbic acid, maleic acid, mandelic acid, and the like. Preferred salts are those formed with hydrohalic acids and especially preferred are those formed with hydrochloric acid and maleic acid. The pharmaceutically acceptable acid addition salts preferably can be prepared in an inert solvent, for example, ethanol, acetone or acetonitrile by treating the free base with the corresponding anhydrous acid.

The bases of formulas I and Ia are crystalline, solid substances which are relatively soluble in dimethylsulfoxide, dimethylformamide or in chlorinated hydrocarbons such as chloroform, methylene chloride or in an alkanol such as methanol or ethanol and are relatively insoluble in water.

The pharmaceutically acceptable acid addition salts of the bases of formulas I and Ia are crystalline, solid substances. They are freely soluble in dimethylsulfoxide and dimethylformamide, in alkanols such as methanol or ethanol, and also in chloroform, methylene chloride and water. The pharmaceutically acceptable addition salts of the bases of formulas I and Ia are relatively insoluble in benzene, ether and petroleum ether.

The compounds of formulas I and Ia are useful as central depressants and neuroleptic agents, substantially devoid of cataleptic activity or effect.

A cataleptic effect ("wax-like rigidity", that is, maintaining for an abnormally long period a forced upon body position) is considered to be a disturbing side effect with central depressants and neuroleptically active compounds and indicates motor disturbances. The products according to the invention have the advantage that they do not have this disturbing side effect or have it only to a very slight extent. To prove the lack of cataleptic activity, representative samples of the end products of the invention were administered intraperitoneally to rats. The following compounds were tested:

Product A: 1-(2-chloro-7-fluoro-10,11-dihydrodibenzo[b,f]thiepin-10-yl)-4-methylpiperazine maleate;

Product B: 1-(3-chloro-8-fluoro-10,11-dihydrodibenzo[b,f]thiepin-10-yl)-4-methylpiperazine maleate; and Product C: 4-(2-chloro-8-fluoro-10,11-dihydrodibenzo[b,f]thiepin-10-yl)-1-piperazinepropanol maleate.

The foregoing compounds were compared to chlorpromazine, a well-known central depressant, especially well known as a neuroleptic agent.

The test animals are considered to be cataleptic when the homolateral extremities remain in the crossed position for at least 10 seconds. The number of cataleptic animals is recorded every 30 minutes over a 6-hour period. The $ED_{50}$ is the dose at which 50% of the animals are cataleptic.

RESULTS

| Product | $ED_{50}$ mg/kg. |
|---|---|
| 1-(2-chloro-7-fluoro-10,11-dihydro-dibenzo[b,f]thiepin-10-yl)-4-methylpiperazine maleate (Product A) | 70 |
| 1-(3-chloro-8-fluoro-10,11-dihydro-dibenzo[b,f]thiepin-10-yl)-4-methylpiperazine maleate (Product B) | 100 |
| 4-(2-chloro-8-fluoro-10,11-dihydro-dibenzo[b,f]thiepin-10-yl)-1-piperazinepropanol maleate (Product C) | 64 |
| Chlorpromazine | 6 |

The data of the table demonstrate that only very weak cataleptic effect is produced by Substances A, B and C of the invention, as compared to chlorpromazine which does demonstrate cataleptic effects.

To demonstrate the central depressant effect, especially the neuroleptic effect of the products of the invention, representative compounds were utilized in the following tests:

I. Rotating Rod Test

In the Rotating Rod Test, the ability of mice to achieve a coordinated motor performance is investigated. After peroral administration of the test substance, the mice are placed upon a horizontal slowly rotating rod and the time they remain off the rod is recorded. The $ED_{50}$ is that dose which reduces the holding on period of the mice by 50% as compared to the holding on period prior to the administration of the test substance.

Product A demonstrates in this test a strong activity ($ED_{50} = 5.8$ mg/kg.) which activity approximates that of chlorpromazine ($ED_{50} = 5$ mg/kg.). Product B ($ED_{50} = 3.1$ mg/kg.) is superior to chlorpromazine.

II. Determination of Homovanillinic Acid

Two hours prior to being killed, rats are injected with the test substance.

Thereafter, the homovanillinic acid is extracted from the supernatant portion of a homogenized mixture of the brains of the treated rats into butyl acetate and later into an aqueous solution and is oxidized with potassium ferric cyanide to a fluorescent dimer. From an increased concentration of homovanillinic acid (HVA), it can be demonstrated that the test substance works the same as chlorpromazine, that is, it increases the turnover of dopamine in the basal ganglions. The homovanillinic acid titer in untreated rats is arbitrarily set at 100%.

RESULTS

| Product | Doses mg/kg. p.o. | Increase in HVA, % |
|---|---|---|
| 1-(2-chloro-7-fluoro-10,11-dihydro-dibenzo[b,f]thiepin-10-yl)-4-methylpiperazine maleate (Product A) | 50 | 280 |
| 4-(2-chloro-8-fluoro-10,11-dihydro-dibenzo[b,f]thiepin-10-yl)-1-piperazinepropanol maleate (Product C) | 50 | 273 |
| Chlorpromazine | 20 | 321 |

In this test, Substances A and C demonstrate an activity which is nearly as potent as that of chlorpromazine.

III. "Pole Climbing" Test

The test provides information regarding the behavioral reactions of rats. Rats are trained to avoid an electrical stimulus (unconditioned stimulation) which is effected through a base grid a few seconds after an acoustical signal (conditioned stimulation) by climbing up a vertical rod in the test chamber.

The blocking of the conditioned reaction is expressed by the parameter $ED_{50}$ (mg/kg. p.o.), the blocking of the unconditioned reaction is expressed by the parameter $ED_{10}$ (mg/kg. p.o.).

The parameter $ED_{50}$ (blocking of conditioned reaction) gives a standard for the potency of the neuroleptic activity of the test substance. The quotient of $ED_{10}$ (blocking of unconditioned reaction)/$ED_{50}$ (blocking of conditioned reaction) gives a standard value for the qualitative effect or activity of the test substance in that as the quotient increases, a stronger selectivity of the neuroleptic effect (lower neurotoxic side effects) is seen. A comparison between Products A and B and chlorpromazine demonstrates the following:

| Product | $ED_{50}$ (Blocking of the conditioned reaction) mg/kg. p.o. | Quotient-$ED_{10}$ (Blocking of the unconditioned reaction)/$ED_{50}$ (Blocking of the conditioned reaction |
|---|---|---|
| 1-(2-chloro-7-fluoro-10,11-dihydro-dibenzo[b,f]-thiepin-10-yl)-4-methyl-piperazine maleate (Product A) | 30 | 3.3 |
| 1-(3-chloro-8-fluoro-10,11-dihydro-dibenzo[b,f]-thiepin-10-yl)-4-methyl-piperazine maleate | | |

-continued

| Product | $ED_{50}$ (Blocking of the conditioned reaction) mg/kg. p.o. | Quotient-$ED_{10}$ (Blocking of the unconditioned reaction)/ $ED_{50}$ (Blocking of the conditioned reaction |
|---|---|---|
| (Product B) | 27 | 11.0 |
| Chlorpromazine | 11.6 | 3.5 |

In this test, the strength of the neuroleptic activity of Substance A is about half that of chlorpromazine, while the quality (selectivity) of the neuroleptic activity is about equal to that of chlorpromazine. The strength of the neuroleptic activity of Substance B is about half of that of chlorpromazine, while the quality (selectivity) of the neuroleptic activity of Substance B is considerably superior to that of chlorpromazine.

The compounds of the invention, i.e., the compounds of formulas I and Ia can be used in the form of pharmaceutical preparations, which contain them or their salts in admixture with organic or inorganic pharmaceutically inert carriers suitable for enteral and parenteral application such as, for example, water, gelatin, gum arabic, lactose, starches, vegetable oils, polyalkyleneglycols, and the like. The pharmaceutical preparations can be in solid form, for example, tablets, dragees, suppositories or capsules or in liquid form, for example, as solutions, suspensions or emulsions. The preparations may be sterilized and/or contain additives such as preservatives, stabilizers, wetting or emulsifying agents or salts for varying the osmotic pressure. The pharmaceutical preparations can also contain additional therapeutically active substances.

Preferably, the pharmaceutical dosage forms contain from about 1 to about 200 mg. of a compound of formula I or Ia or an equivalent amount of their respective salts. Preferably, the oral dosage range is between about 0.1 mg./kg/day to about 7.5 mg/kg/day. A preferable dosage range for parenteral preparations is between about 0.01 mg/kg/day to about 0.75 mg/kg/day. It is understood, however, that the above-mentioned ranges can be varied according to the individual needs and the prescription of the practitioner.

As is evident, the compounds of formulas I and Ia and their pharmaceutically acceptable acid addition salts have effects qualitatively similar to those of chlorpromazine, known for its therapeutic uses and properties. Thus, the compounds of the invention demonstrate a pattern of activity associated with neuroleptic agents of known efficacy and safety.

The following Examples further illustrate the invention. All temperatures are in degrees Centigrade, unless otherwise mentioned.

EXAMPLE 1

Preparation of 1-(8-fluoro-10,11-dihydro-2-methyl-dibenzo[b,f]thiepin-10-yl)-4-methyl-piperazine 75 G. of 10-chloro-8-fluoro-10,11-dihydro-2-methyl-dibenzo[b,f]-thiepin are heated together with 150 ml. of N-methyl-piperazine at 130° for 10 minutes. Thereafter, the mixture is cooled to 40°, mixed with ice, benzene and aqueous sodium hydroxide solution and again mixed well. The benzene phase is acidified with 6N hydrochloric acid and maintained in an ice bath for 30 minutes. The precipitate is filtered, made alkaline with aqueous sodium hydroxide solution and taken up in benzene. The benzene phase is dried over sodium sulfate and evaporated, whereby 1-(8-fluoro-10,11-dihydro-2-methyl-dibenzo[b,f]-thiepin-10-yl)-4-methyl-piperazine is formed and is treated with maleic acid and the corresponding maleate is formed. The maleate has a melting point of 173°–174°.

The starting material 10-chloro-8-fluoro-10,11-dihydro-2-methyl-dibenzo[b,f]thiepin can be prepared as follows:

A solution of 474.5 g. of potassium hydroxide in 3.6 l. of water is reacted under an atmosphere of nitrogen at 50° with 217 ml. of 4-fluoro-(thiophenol) and mixed at room temperature for 15 minutes. After the addition of 1 g. of copper powder and 536 g. of 2-iodo-5-methylbenzoic acid, the mixture is heated under reflux conditions for 7 hours. The reaction mixture is filtered hot, acidified with hydrochloric acid and filtered again. The residue is washed neutral with water and evaporated under reduced pressure, whereby 3-methyl-6-[(4'-fluorophenyl)thio]-benzoic acid is obtained and has a melting point of 166°–167°.

300 G. of 3-methyl-6-[(4'-fluorophenyl)-thio]-benzoic acid in 2 l. of absolute tetrahydrofuran are reacted dropwise under an atmosphere of nitrogen and under reflux conditions with 780 ml. of a 70% sodium dihydro-bis-(2-methoxyethoxy)-aluminate solution in benzene and heated for an additional 1 hour under reflux conditions. The reaction mixture is cooled to 4°, acidified dropwise with 1,300 ml. of 3N hydrochloric acid, then mixed with concentrated hydrochloric acid and extracted with benzene. The organic phase is washed with water, dried over sodium sulfate, filtered and evaporated, whereby there is obtained 3-methyl-6-[4'-fluorophenyl)-thio]-benzyl alcohol as a yellow oil.

337 G. of 3-methyl-6-[(4'-fluorophenyl)-thio]-benzyl alcohol are dissolved in 1 l. of absolute benzene and maintained at reflux temperature. The solution is treated dropwise with 190 ml. of thionyl chloride and heated for an additional 45 minutes. This reaction mixture is evaporated under reduced pressure. The residue is again extracted with benzene, the benzene is evaporated, whereby there is obtained 3-mehyl-6-[(4'-fluorophenyl)-thio]-benzyl chloride as a brown oil.

115 G. of potassium cyanide in 150 ml. of water are heated together with 344 g. of 3-methyl-6-[(4'-fluorophenyl)-thio]-benzyl chloride in 450 ml. of ethanol under reflux conditions over a period of 10 hours. The ethanol is thereafter distilled under reduced pressure. The residue is diluted water water and extracted with benzene. The benzene phase is again washed with water, dried over sodium sulfate and evaporated, whereby there is obtained 3-methyl-6-[(4'-fluorophenyl)-thio]-phenylacetonitrile as a dark brown oil.

106 G. of 3-methyl-6-[(4'-fluorophenyl)-thio]-phenylacetonitrile, 300 ml. of ethanol, 100 g. of potassium hydroxide and 300 ml. of water are heated together under reflux conditions over a period of 5 hours. Thereafter, the ethanol is evaporated under reduced pressure. The residue is dissolved in water and the neutral portion extracted with benzene. The aqueous solution is acidified with concentrated hydrochloric acid and extracted with ethyl acetate. The organic phase is washed with water, dried over sodium sulfate, filtered and evaporated under reduced pressure, whereby there is obtained 3-methyl-6-[(4'-fluorophenyl)thio]-phenyl acetic acid as a dark brown oil, which after recyrstallization from benzene/hexane, has a melting point of 117°.

1,810 G. of polyphosphoric acid are heated under an atmosphere of nitrogen to 128°, then quickly there is mixed therewith 173.6 g. of 3-methyl-6-[(4'-fluorophenyl)-thio]-phenyl acetic acid and the mixture is stirred at 120°–130° for 10 minutes. After the addition of crushed ice, the mixture is extracted with benzene. The organic phase is again washed with water with a saturated aqueous sodium carbonate solution, dried over sodium sulfate and evaporated, whereby there is obtained 8-fluoro-2-methyl-dibenzo[b,f]-thiepin-10(11H)-one, which has a melting point of 103°–104°.

103 G. of 8-fluoro-2-methyl-dibenzo[b,f]-thiepin-10(11H)-one are suspended in 550 ml. of ethanol and mixed with 24.3 g. of sodium borohydride. The reaction mixture is heated for about 10 minutes under reflux conditions. The reaction mixture, after the addition of water, is extracted with chloroform. The organic phase is again washed with water, dried over sodium sulfate and evaporated, whereby there is obtained 8-fluoro-10,11-dihydro-2-methyl-dibenzo-[b,f]-thiepin-10-ol as an oil.

103 G. of 8-fluoro-10,11-dihydro-2-methyl-dibenzo[b,f]thiepin-10-one, 500 ml. of benzene and 38.4 g. of finely pulverized calcium chloride are saturated with hydrochloric acid gas at 15° and stirred overnight. The residue is filtered, washed with benzene and evaporated under reduced pressure, whereby there is obtained 10-chloro-8-fluoro-10,11-dihydro-2-methyl-dibenzo[b,f]thiepin, having a melting point of 63°–64°.

EXAMPLE 2

Preparation of
1-[2-fluoro-10,11-dihydro-8-(methylthio)-dibenzo[b,f]thiepin-10-yl]-4-piperazine 10 G. of 10-chloro-2-fluoro-10,11-dihydro-8-(methylthio)-dibenzo[b,f]thiepin are heated together with 4.56 g. of N-methyl-piperazine on a water bath for 15 minutes. After the reaction mixture is cooled, it is dluted with water and extracted with chloroform. The organic phase is washed well with water and subsequently treated with 2N hydrochloric acid. The resulting precipitate, together with the acid solution, are extracted with ether, and subsequently made alkaline. The alkaline solution is extracted with ether. The organic phase is again washed with water, dried over magnesium sulfate and evaporated. The resulting 1-[2-fluoro-10,11-dihydro-8-(methylthio)-dibenzo[b,f]thiepin-10-yl]-4-methyl-piperazine is reacted with maleic acid and the corresponding maleate obtained which melts at 150°–151°.

The starting material 10-chloro-2-fluoro-10,11-dihydro-8-(methylthio)dibenzo[b,f]thiepin can be prepared from 5-fluoro-2-iodo-benzoic acid and 4-(methylthio)-thiophenol in a similar manner to that described in Example 1. There are obtained as intermediates the following compounds:

3-fluoro-6-{[4'-(methylthio)-phenyl]-thio}-benzoic acid, having a melting point of 184°–185°;

3-fluoro-6-{[4'-(4-methylthio)-phenyl]-thio}-benzyl alcohol as a dark brown oil;

3-fluoro-6-{[4'-(methylthio)-phenyl]-thio}-benzyl chloride as a light brown oil;

3-fluoro-6-{[4'-(methylthio)-phenyl]-thio}-phenylacetonitrile as a dark brown oil;

3-fluoro-6-{[4'-(methylthio)-phenyl]-thio}-phenyl acetic acid having a melting point of 106°–107° after recrystallization from benzene/hexane;

2-fluoro-8-(methylthio)-dibenzo[b,f]thiepin-10(11H)-one having a melting point of 166°–167°; and 2-fluoro-10,11-dihydro-8-(methylthio)-dibenzo[b,f]-thiepin having a melting point of 116°–117°.

The obtained 10-chloro-2-fluoro-10,11-dihydro-8-(methylthio)-dibenzo[b,f]thiepin melts at 112°.

EXAMPLE 3

Preparation of
1-(2-chloro-7-fluoro-10,11-dihydro-dibenzo[b,f]thiepin-10-yl)-4-methyl-piperazine.

12 g of 2,10-dichloro-7-fluoro-10,11-dihydro-dibenzo[b,f]thiepin are heated for 10 minutes together with 16 g of N-methylpiperazine at an external temperature of 120°–130°. After cooling the reaction mixture is poured on water and extracted with ether. The organic phase is washed with water and subsequently treated with 2 N hydrochloric acid. A precipitate is obtained. The mixture is extracted with ether, made alkaline and subsequently again extracted with ether. The organic phase is washed with water, dried over magnesium sulphate and evaporated. The so-obtained raw 1-(2-chloro-7-fluoro-10,11-dihydro-dibenzo[b,f]thiepin-10-yl)-4-methylpiperazine is converted to the corresponding maleate by treatment with maleic acid. The maleat melts at 200° with decomposition.

The starting material 2,10-dichloro-7-fluoro-10,11-dihydro-dibenzo[b,f]thiepin can be prepared from 2-iodo-5-chlorobenzoic acid and 3-fluoro-(thiophenol) in a similar manner to that described in example 1. The following compounds are obtained as intermediates:

3-chloro-6-[(3'fluoro-phenyl)-thio]-benzoic acid; melting point 171°–173°.

3-chloro-6-[(3'-fluoro-phenyl)-thio]-benzyl alcohol (brown oil).

3-chloro-6-[(3'-fluoro-phenyl)-thio]-benzyl chloride (brown oil).

3-chloro-6-[(3'-fluoro-phenyl)-thio]-phenyl acetonitrile.

3-chloro-6-[(3'-fluoro-phenyl)-thio]-phenyl acetic acid; melting point after recrystallisation from acetone/hexane, 124°–126°.

2-chloro-7-fluoro-dibenzo[b,f]thiepin-10(11H)-on; melting point 117.5°–118.5°.

2-chloro-7-fluoro-10,11-dihydro-dibenzo[b,f]thiepin-10-ol; melting point 98°–99°.

The obtained 2,10-dichloro-7-fluoro-10,11-dihydrodibenzo[b,f]thiepin melts at 119°–120°.

EXAMPLE 4

In the same manner as described in example 3, starting from 2,10-dichloro-8-fluoro-10,11-dihydro-dibenzo[b,f]thiepin and N-methylpiperazine, there is obtained 1-[2-chloro-8-fluoro-10,11-dihydro-dibenzo[b,f]thiepin-10-yl]-4-methyl-piperazine which melts at 118°–120°. After recrystallisation of this base from ether and reaction with maleic acid the corresponding maleate is obtained which melts at 174°–175°.

The starting material 2,10-dichloro-8-fluoro-10,11-dihydrodibenzo[b,f]thiepin can be prepared from 5-chloro-2-iodobenzoic acid and 4-fluoro-(thiophenol) in a similar manner to that described in example 1. The following intermediates are obtained:

3-chloro-6-[(4'-fluoro-phenyl)-thio]-benzoic acid; melting point 176°–177°.
3-chloro-6-[(4'-fluoro-phenyl)-thio]-benzyl alcohol (brown oil).
3-chloro-6-[(4'-fluoro-phenyl)-thio]-benzyl chloride (brown oil).
3-chloro-6-[(4'-fluoro-phenyl)-thio]-phenyl acetonitrile (dark brown oil).
3-chloro-6-[(4'-fluoro-phenyl)-thio]-phenyl acetic acid; melting point after recrystallisation from benzene/hexane 93°.
2-chloro-8-fluoro-dibenzo[b,f]thiepin-10(11H)-one. melting point 132°.
2-chloro-8-fluoro-10,11-dihydro-dibenzo[b,f]thiepin-10-ol; melting point 90°.

The obtained 2,10-dichloro-8-fluoro-10,11-dihydrodibenzo[b,f]thiepin consists of white crystals melting at 84°–85°.

EXAMPLE 5

If the N-methylpiperazine in Example 4 is replaced by N-hydroxypropylpiperazine, there is obtained, under otherwise similar conditions, 4-(2-chloro-8-fluoro-10,11-dihydro-dibenzo[b,f]thiepin-10-yl)-1-piperazinyl-propanol, melting at 136°–138° The base is converted to the corresponding maleate by reaction with maleic acid. The maleate melts at 178°.

EXAMPLE 6

18.25 g of 3,10-dichloro-8-fluoro-10,11-dihydro-dibenzo[b,f]thiepin are heated for 10 minutes together with 26.2 g of N-methylpiperazine at an external temperature of 120°–130°. After cooling the reaction mixture is poured on water and extracted with ether. The organic phase is washed with water and extracted with dilute aqueous methane sulfonic acid. The acidic aqueous solution is extracted with ether, made alkaline and again extracted with ether. The organic phase is washed with water, dried over magnesium sulfate and evaporated. The so-obtained 1-(3-chloro-8-fluoro-10,11-dihydrodibenzo[b,f]thienpin-10-yl)-4-methyl-piperazine melts, after recrystallisation from acetone, at 133°–135°. The base is converted to the corresponding maleate by reaction with maleic acid. The maleate melts at 168°–169°.

The starting material 3,10-dichloro--fluoro--fluoro10,11-dihydro-dibenzo[b,f]thiepin can be prepared from 4-chloro-2-iodobenzoic acid and 4-fluoro-(thiophenol) in a similar manner to that described in example 1. The following intermediates are obtained:

4-chloro-6-[(4'-fluoro-phenyl)-thio]-benzoic acid; melting point 212°–214°.
4-chloro-6-[(4'-fluoro-phenyl)-thio]-benzyl alcohol; melting point 86°–87°.
4-chloro-6-[(4'-fluoro-phenyl)-thio]-benzyl chloride (brown oil).
4-chloro-6-[(4'-fluoro-phenyl)-thio]-phenyl acetonitrile (dark brown oil).
4-chloro-6-[(4'-fluoro-phenyl)-thio]-phenyl acetic acid; melting point after recrystallisation from benzene/hexane 96°–100°.
3-chloro-8-fluoro-dibenzo[b,f]thiepin-10(11H)-one. melting point 160°–161°.
3-chloro-8-fluoro-10,11-dihydro-dibenzo[b,f]thiepin-10-ol; melting point 115°–117°.

The obtained 3,10-dichloro-8-fluoro-10,11-dihydro-dibenzo[b,f]thiepin melts at 133.5°–135°.

EXAMPLE 7

13 g of 2,10-dichloro-7-fluoro-10,11-dihydro-dibenzo[b,f]thiepin are heated for 10 minutes together with 25 g of N-hydroxypropylpiperazine at an external temperature of 120°–130°. After cooling the reaction mixture is poured on water and extracted with ether. The organic phase is washed with water and treated with 2 N aqueous hydrochloric acid. A precipitate is obtained. This precipitate is extracted, together with the acidic solution, with ether, made alkaline and subsequently extracted with benzene. The organic phase is washed with water, dried over magnesium sulfate and evaporated. The residue is chromatographed over aluminum oxide with benzene and chloroform. The so-obtained 4-(2-chloro-7-fluoro-10,11-dihydro-dibenzo[b,f]thiepin-10-yl)-1-piperazinylpropanol is converted to the corresponding maleate be reaction with maleic acid. The maleate melts at 95°–97°.

EXAMPLE 8

18.6 g of 10-chloro-8-fluoro-10,11-dihydro-2-methyldibenzo[b,f]thiepin are heated together with 35 g of N-hydroxyethylpiperazine for 8 minutes at a temperature of 130°. The product is worked up as described in example 1; one obtains 4-(8-fluoro-10,11-dihydro-2-methyl-dibenzo[b,f]thiepin-10-yl)-1-piperazinylethanol which is converted to the corresponding dihydrochloride by treatment with ethanolic hydrochloric acid. The dihydrochloride melts at 228°–230°C with decomposition.

EXAMPLE 9

18 g of 8-fluoro-2-methyl-dibenzo[b,f]thiepin-10(11H)-one in 140 ml of absolute benzene are together with 33.2 ml of N methylpiperazine within ½ hour at 20°–25° treated with a solution of 5.8 ml of titanium tetrachloride in 40 ml of absolute benzene. The reaction mixture is subsequently heated for 20 hours under reflux conditions. The reaction mixture is poured, with vigorous stirring, into a mixture of 40 ml of saturated aqueous sodium bicarbonate solution and 120 ml of water, subsequently filtered and extracted with chloroform. The organic phase is dried and evaporated. One obtains 1-(8-fluoro-2-methyl-dibenzo[b,f]-thiepin-10-yl)-4-methyl-piperazine, which is converted into the corresponding maleate by treatment with maleic acid. The maleate melts at 244° with decomposition.

EXAMPLE 10

Preparation of
1-{8-fluoro-10,11-dihydro-3-methyl-dibenzo[b,f]thiepin-10-yl{-4-methylpiperazine 10.6 g. of 10-chloro-8-fluoro-10,11-dihydro-3-methyldibenzo[b,f]thiepin, 200 ml. of chloroform and 11.4 g. of N-methylpiperazine are heated at reflux for 30 hours. The mixture is evaporated under reduced pressure. The resulting residue is worked up via the neutral portion in essentially the same manner as described in Example 1, and there is obtained 1-{8- fluoro-10,11-dihydro-3-methyl-dibenzo[b,f]thiepin-10-yl}-4-methylpiperazine, having a melting point of 117°–121°C. By treatment with methanesulfonic acid, there is obtained the dimethanesulfonate having a melting point of 176°–178°C. (from methanol/ether).

The 10-chloro-8-fluoro-10,11-dihydro-3-methyl-dibenzo[b,f]thiepin used as the starting material can be prepared in an analogous manner to that described in Example 1. The following intermediates are obtained in the reaction:

- 4-methyl-6-[(4'-fluorophenyl)-thio]-benzoic acid, having a melting point of 185°–186°C.;
- 4-methyl-6-[(4'-fluorophenyl)-thio]-benzyl alcohol (orange oil);
- 4-methyl-6-[(4'-fluorophenyl)-thio]-benzyl chloride (red-brown oil);
- 4-methyl-6-[(4'-fluorophenyl)-thio]-phenylacetonitrile (brown oil);
- 4-methyl-6-[(4'-fluorophenyl)-thio]-phenylacetic acid having a melting point of 135°–137°C. from acetone/low boiling petroleum ether;
- 8-fluoro-3-methyl-dibenzo[b,f]thiepin-10(11H)-one having a melting point of 96°–99°C. from ethanol; and
- 8-fluoro-3-methyl-10,11-dihydro-dibenzo [b,f]thiepin-10-ol (brown oil).

The 10-chloro-8-fluoro-10,11-dihydro-3-methyl-dibenzo[b,f]thiepin obtained is a brown oil which crystallizes upon standing.

EXAMPLE 11

Preparation of
1-{3-chloro-7-fluoro-10,11-dihydro-dibenzo[b,f]thiepin-10-yl}-4-methylpiperazine -4

13 g. of 3,10-dichloro-7-fluoro-10,11-dihydro-dibenzo[b,f]thiepin are treated with 17.7 g. of N-methylpiperazine and stirred for 10 minutes at 120°–130°C. (internal temperature). Then, the mixture is treated with 2N sodium hydroxide and extracted with ether. The organic phase is washed neutral with water and extracted with 1N methanesulfonic acid. The acidic solution is made alkaline and extracted with ether. The ether solution is washed with water, dried over magnesium sulfate and concentrated in a vacuum, and there is obtained, as a crude oil, 1-{3-chloro-7-fluoro-10,11-dihydro-dibenzo[b,f]thiepin-10-yl}-4-methylpiperazine which is converted into the maleate having a melting point of 156°–158°C. by treatment with maleic acid.

The 3,10-dichloro-7-fluoro-10,11-dihydro-dibenzo[b,f]thiepin used as the starting material can be prepared starting from 4-chloro-2-iodo-benzoic acid and 3-fluoro-thiophenol in an analogous manner to that described in Example 1. The following intermediates are obtained in the reaction:

- 4-chloro-2-[(3'-fluorophenyl)-thio]-benzoic acid having a melting point of 183°–185°C.;
- 4-chloro-2-[(3'-fluorophenyl)-thio]-benzyl alcohol (oil);
- 4-chloro-2-[(3'-fluorophenyl)-thio]-benzyl chloride (oil);
- 4-chloro-2-[(3'-fluorophenyl)-thio]-phenylacetonitrile (oil);
- 4-chloro-2-[(3'-fluorophenyl)-thio]-phenylacetic acid having a melting point of 117°–119°C.;
- 3-chloro-7-fluoro-dibenzio[b,f]thiepin-10(11H)-one having a melting point of 145°–148°C.; and
- 3-chloro-7-fluoro-10,11-dihydro-dibenzo[b,f]thiepin-10-ol having a melting point of 103°–105°C.

The 3,10-dichloro-7-fluoro-10,11-dihydro-dibenzo[b,f]thiepin obtained melts at 117°–118°C.

EXAMPLE 12

Preparation of
1-{8-fluoro-10,11-dihydro-3-methoxy-dibenzo[b,f]-thiepin-10-yl}-4-methylpiperazine 12 G. of 10-chloro-8-fluoro-10,11-dihydro-3-methoxy-dibenzo[b,f]thiepin are treated with 16.3 g. of N-methylpiperazine and stirred for 10 minutes at 100°–120°C. (internal temperature). Thereafter, the mixture is cooled and treated with 2N sodium hydroxide. The mixture is then extracted with ether and the organic phase washed with water. The ether solution is extracted with dilute methanesulfonic acid and the acidic solution made alkaline with sodium hydroxide and extracted with methylene chloride. The organic phase is washed with water, dried over magnesium sulfate and concentrated, and there is obtained 1-{8-fluoro-10,11-dihydro-3-methoxy-dibenzo[b,f]thiepin-10-yl}-4-methylpiperazine having a melting point of 141°–144°C. This base is converted by treatment with methanesulfonic acid into the methanesulfonate which has a melting point of 208°–210°C.

The 10-chloro-8-fluoro-10,11-dihydro-3-methoxy-dibenzo[b,f]thiepin used as the starting material can be prepared starting from 2-iodo-4-methoxy-benzoic acid and 4-fluoro-thiophenol in an analogous manner to that described in Example 1. The following intermediates are obtained in the reaction:

- 4-methoxy-2-[(4'-fluorophenyl)-thio]-benzoic acid having a melting point of 200°–202°C.;
- 4-methoxy-2-[(4'-fluorophenyl)-thio]-benzyl alcohol (yellow oil);
- 4-methoxy-2-[(4'-fluorophenyl)-thio]-benzyl chloride (brown oil);
- 4-methoxy-2-[(4'-fluorophenyl)-thio]-phenylacetonitrile (brown oil);
- 4-methoxy-2-[(4'-fluorophenyl)-thio]-phenylacetic acid having a melting point of 78°–81°C.;
- 8-fluoro-3-methoxy-dibenzo[b,f]thiepin-10(11H)-one having a melting point of 112°–114°C.; and
- 8-fluoro-10,11-dihydro-3-methoxy-dibenzo[b,f]thiepin-10-ol (yellow oil).

The 10-chloro-8-fluoro-10,11-dihydro-3-methoxy-dibenzo[b,f]thiepin obtained melts at 74°–76°C.

EXAMPLE 13

Preparation of
1-{8-fluoro-10,11-dihydro-3-trifluoromethyldibenzo[b,f]thiepin-10-yl}-4-methylpiperazine 9 G. of 10-chloro-8-fluoro-10,11-dihydro-3-trifluoromethyldibenzo[b,f]thiepin are treated with 11 g. of N-methylpiperazine and stirred for 10 minutes at 105°–110°C. The cooled mixture is treated with 2N sodium hydroxide and extracted with ether. The ether solution is washed neutral with water and shaken with dilute methanesulfonic acid. The acidic solution is made alkaline with sodium hydroxide and extracted with ether. The organic phase is washed with water, dried over magnesium sulfate and evaporated in a vacuum, and there is obtained 1-{8-fluoro-10,11-dihydro-3-trifluoromethyl-dibenzo[b,f]thiepin-10-yl}-4-methylpiperazine as a yellow oil which is converted into the methanesulfonate having a melting point of 224°–226°C. by treatment with methanesulfonic acid.

The 10-chloro-8-fluoro-10,11-dihydro-2-trifluoromethyldibenzo[b,f]thiepin used as the starting material can be prepared starting from 2-iodo-4-trifluoromethyl-benzoic acid and 4-fluoro-thiophenol in an analogous manner to that described in Example 1. The following intermediates are obtained in the reaction:

2-[(4'-fluorophenyl)-thio]-4-trifluoromethyl-benzoic acid having a melting point of 161°–163°C.;

2-[(4'-fluorophenyl)-thio]-4-trifluoromethyl-benzyl alcohol having a boiling point of 108°–125°C./0.10 mmHg and a melting point of 53.5°–55°C.;

2-[(4'-fluorophenyl)-thio]-4-trifluoromethyl-benzyl chloride (oil);

2-[(4'-fluorophenyl)-thio]-4-trifluoromethyl-phenylacetonitrile having a boiling point of 114°–120°C./0.3 mmHg;

2-[(4'-fluorophenyl)-thio]-4-trifluoromethyl-phenylacetic acid having a melting point of 117°–119°C.;

8-fluoro-3-trifluoromethyl-dibenzo[b,f]thiepin-10(11H)-one having a melting point of 88°–89°C.; and 8-fluoro-10,11-dihydro-3-trifluoromethyl-dibenzo]b,f]-thiepin-10-ol (yellow oil).

The 10-chloro-8-fluoro-10,11-dihydro-3-trifluoromethyldibenzo[b,f]thiepin obtained melts at 73°–75°C.

The Examples which follow illustrate typical pharmaceutical preparations containing the dibenzo[b,f]thiepin derivatives of the invention.

| Example A TABLETS | Per Tablet |
|---|---|
| 1-{3-chloro-8-fluoro-10,11-dihydro-dibenzo[b,f]thiepin-10-yl}-4-methylpiperazine maleate | 100 mg. |
| Lactose | 202 mg. |
| Maize Starch | 80 mg. |
| Hydrolyzed Maize Starch | 20 mg. |
| Calcium Stearate | 8 mg. |
| Total Weight | 410 mg. |

The active ingredient, lactose, maize starch and hydrolyzed maize starch are mixed together and granulated to a viscous paste with water. The paste is passed through a sieve and subsequently dried overnight at 45°C. The dried granulate is again passed through a sieve and then mixed with the calcium stearate. The mixture obtained is pressed into tablets having a weight of 410 mg. and a diameter of about 10 mm.

| Example B TABLETS | Per Tablet |
|---|---|
| 1-{3-chloro-8-fluoro-10,11-dihydro-dibenzo[b,f]thiepin-10-yl}-4-methylpiperazine maleate | 25.0 mg. |
| Lactose | 114.0 mg. |
| Maize Starch | 50.0 mg. |
| Gelatinized maize starch | 8.0 mg. |
| Calcium Stearate | 3.0 mg. |
| Total Weight | 200.0 mg. |

The active ingredient, lactose, maize starch and gelatinized maize starch are intimately mixed with one another. The mixture is passed through a comminuting machine and subsequently moistened with water to a thick paste. The moist mass is passed through a sieve. The moist granulate is dried a 45°C. The dried granulate is mixed thoroughly with the calcium stearate and then is passed into tablets having a weight of 200 mg. and a diameter of about 8 mm.

| Example C TABLETS | Per Tablet |
|---|---|
| 1-{3-chloro-8-fluoro-10,11-dihydro-dibenzo[b,f]thiepin-10-yl}-4-methylpiperazine maleate | 14.5 mg. |
| Lactose | 124.5 mg. |
| Maize Starch | 50.0 mg. |
| Gelatinized Maize Starch | 8.0 mg. |
| Calcium Stearate | 3.0 mg. |
| Total Weight | 200.0 mg. |

The active ingredient, lactose, maize starch and gelatinized maize starch are intimately mixed with one another. The mixture is passed through a comminuting machine and subsequently moistened with water to a thick paste. The moist mass is passed through a sieve. The moist granulate is dried at 45°C. and thereafter is thoroughly mixed with the calcium stearate. The granulate is then pressed into tablets having a weight of 200 mg. and a diameter of about 8 mm.

| Example D TABLETS | Per Tablet |
|---|---|
| 1-{3-chloro-8-fluoro-10,11-dihydro-dibenzo[b,f]thiepin-10-yl}-4-methylpiperazine maleate | 25.00 mg. |
| Lactose | 110.00 mg. |
| Maize Starch | 61.00 mg. |
| Talc | 3.40 mg. |
| Magnesium Stearate | 0.60 mg. |
| Total Weight | 200.00 mg. |

The ingredients are intimately mixed with one another and pressed into tablets weighing 200 mg. The tablets are subsequently coated with ethyl cellulose and Carbowax.

| Example E CAPSULES | Per Capsule |
|---|---|
| 1-{3-chloro-8-fluoro-10,11-dihydro-dibenzo[b,f]thiepin-10-yl}-4-methylpiperazine maleate | 29.0 mg. |
| Lactose | 156.0 mg. |
| Maize Starch | 30.0 mg. |
| Talc | 5.0 mg. |
| Total capsule content | 220.0 mg. |

The active ingredient, lactose and maize starch are intimately mixed with one another and passed through a comminuting machine. The mixture is then thoroughly mixed with the talc and filled into hard gelatin capsules.

| Example F CAPSULES | Per Capsule |
|---|---|
| 1-{3-chloro-8-fluoro-10,11-dihydro-dibenzo[b,f]thiepin-10-yl}-4- | |

21
-continued

Example F
CAPSULES

| | Per Capsule |
|---|---|
| methylpiperazine 25.5 mg. | |
| Lactose | 159.5 mg. |
| Maize Starch | 30.0 mg. |
| Talc | 5.0 mg. |
| Total capsule content | 220.0 mg. |

The active ingredient, lactose and maize starch are intimately mixed with one another and passed through a comminuting machine. The mixture is then thoroughly mixed with the talc and filled into hard gelatin capsules.

Example G
PARENTERAL FORMULATION

| Each 1 ml. ampule contains: | |
|---|---|
| 1-{3-chloro-8-fluoro-10,11-dihydro-dibenzo[b,f]thiepin-10-yl}-4-methylpiperazine maleate | 10.20 mg. (2 percent excess) |
| Methanesulfonic acid for injection | 2.22 mg. |
| Glucose for injection | 40.0 mg. |
| Water for injection q.s. ad | 1.0 ml |

22.2 G. of methanesulfonic acid for injection, 102 g. of active ingredient and 400 g. of glucose are successively dissolved in 8000 ml. of water for injection in a glass vessel with stirring at room temperature. Subsequently, additional water for injection is added up to a total volume of 10,000 ml. The solution is either filtered sterile, filled into colorless ampules, gassed with nitrogen and sealed or filled into colorless ampules, gassed with nitrogen, sealed and subsequently sterilized for 30 minutes with a current of steam or autoclaved at 120°C.

It will be appreciated that in place of the active ingredients mentioned in Examples A to G hereinbefore similar pharmaceutical preparations containing other of the dibenzo[b,f]thiepin derivatives of the invention can also be prepared. Thus, for example, pharmaceutical preparations containing the following derivatives can be prepared:

1-{2-chloro-7-fluoro-10,11-dihydro-dibenzo[b,f]-thiepin-10-yl}-4-methylpiperazine or the maleate thereof;

4-{2-chloro-8-fluoro-10,11-dihydro-dibenzo[b,f]-thiepin-10-yl}-1-piperazinopropanol or the maleate thereof and 1-{8-fluoro-10,11-dihydro-2-methyl-dibenzo[b,f]-thiepin-10-yl}-4-methylpiperazine or the maleate thereof.

Exemplary of additional end products encompassed by claim 1 are the following:

1-(8-fluoro-3-methoxy-10,11-dihydro-dibenzo[b,f]-thiepin-10-yl)-4-methylpiperazine;

1-(8-dimethylsulfamoyl-3-fluoro-10,11-dihydro-dibenzo[b,f]thiepin-10-yl)-4-methylpiperazine;

and their pharmaceutically acceptable acid addition salts;

The compounds corresponding to the end products of Examples 1-13 and to the above compounds which are 4-(3-hydroxypropyl)-piperazines or 4-(3-decanoyloxypropyl)-piperazines instead of 4-methyl-piperazines.

22

I claim:
1. A Compound of the formula

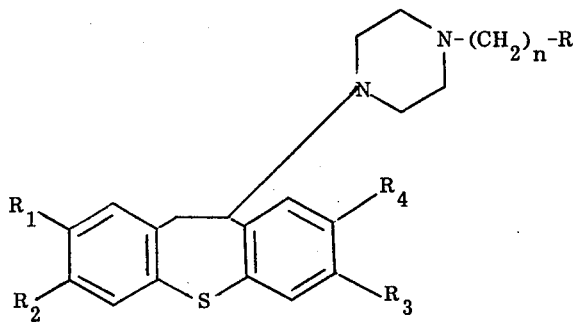

wherein $n$ is an integer from 1 to 3; R is hydrogen or, when $n$ is 2 or 3, is hydroxy or an alkanoyloxy group of 2–18 carbon atoms; one of $R_1$ and $R_2$ is hydrogen and the other is methyl, methoxy, methylthio, dimethylsulfamoyl, fluoro, chloro or trifluoromethyl; and one of $R_3$ and $R_4$ is hydrogen, and the other is methyl, methoxy, methylthio, dimethylsulfamoyl, fluoro, chloro or trifluoromethyl, provided that at least one of $R_1$, $R_2$, $R_3$ and $R_4$ is fluoro, or a pharmaceutically acceptable acid addition salt thereof.

2. A compound in accordance with claim 1, wherein $R_3$ is chloro and $R_4$ is fluoro.

3. A compound in accordance with claim 1, wherein $R_1$ or $R_2$ is methyl, methoxy, methylthio, dimethylsulfamoyl or trifluoromethyl, and $R_3$ or $R_4$ is fluoro.

4. A compound in accordance with claim 3, wherein the group —$(CH_2)_n$—R is methyl or hydroxypropyl.

5. A compound in accordance with claim 1, 1-(2-chloro-7-fluoro-10,11-dihydro-dibenzo[b,f]thiepin-10-yl)-4-methylpiperazine.

6. A compound in accordance with claim 1, 1-(3-chloro-8-fluoro-10,11-dihydro-dibenzo[b,f]thiepin-10-yl)-4-methylpiperazine.

7. A compound in accordance with claim 1, 4-(2-chloro-8-fluoro-10,11-dihydro-dibenzo[b,f]thiepin-10-yl)-1-piperazinepropanol.

8. A compound in accordance with claim 1, 1-(8-fluoro-10,11-dihydro-2-methyl-dibenzo[b,f]thiepin-10-yl)-4-methylpiperazine.

9. A compound in accordance with claim 1, wherein $R_3$ or $R_4$ is fluoro.

* * * * *